United States Patent
Sinha et al.

(10) Patent No.: US 9,222,822 B2
(45) Date of Patent: Dec. 29, 2015

(54) OIL SENSOR

(75) Inventors: Karn R. Sinha, Derby (GB); Nicholas P. Davis, Derby (GB)

(73) Assignee: ROLLS-ROYCE plc, London (GB)

(*) Notice: Subject to any disclaimer, the term of this patent is extended or adjusted under 35 U.S.C. 154(b) by 449 days.

(21) Appl. No.: 13/591,856

(22) Filed: Aug. 22, 2012

(65) Prior Publication Data

US 2013/0068015 A1    Mar. 21, 2013

(30) Foreign Application Priority Data

Sep. 20, 2011  (GB) .................................. 1116173.4

(51) Int. Cl.
*G01F 23/26* (2006.01)
*G01N 33/28* (2006.01)
*G01N 27/02* (2006.01)

(52) U.S. Cl.
CPC ............ *G01F 23/266* (2013.01); *G01F 23/263* (2013.01); *G01F 23/268* (2013.01); *G01N 27/028* (2013.01); *G01N 33/2888* (2013.01)

(58) Field of Classification Search
CPC ... G01N 27/02; G01N 27/06; G01N 33/2888; G01N 27/22; G01N 27/221; G01N 27/028; G01F 23/263; G01F 23/268; G01F 23/266; G01F 23/00; G01F 23/242; G01F 23/0023; G01F 23/243
USPC ......... 73/304 C, 53.05, 114.55, 290 R, 19.11, 73/1.73, 304 R; 324/654, 713, 681
See application file for complete search history.

(56) References Cited

U.S. PATENT DOCUMENTS

| | | | |
|---|---|---|---|
| 4,412,450 A | * | 11/1983 | Franz et al. ................ 73/304 C |
| 4,517,547 A | | 5/1985 | Gray et al. |
| 4,646,070 A | | 2/1987 | Yasuhara et al. |
| 4,733,556 A | | 3/1988 | Meitzler et al. |
| 4,741,204 A | | 5/1988 | Luck et al. |
| 5,089,780 A | | 2/1992 | Megerle |
| 5,274,335 A | | 12/1993 | Wang et al. |
| 5,789,665 A | | 8/1998 | Voelker et al. |

(Continued)

FOREIGN PATENT DOCUMENTS

| DE | 102 55 943 A1 | 6/2004 |
|---|---|---|
| FR | 2 737 297 A1 | 1/1997 |

(Continued)

OTHER PUBLICATIONS

Dec. 23, 2011 British Search Report issued in Application No. 1116173.4.

(Continued)

*Primary Examiner* — John Fitzgerald
*Assistant Examiner* — Marrit Eyassu
(74) *Attorney, Agent, or Firm* — Oliff PLC (57) ABSTRACT

A system and method for measuring oil level and quality is provided. The system and method uses an alternating current (AC) to determine oil level, and a lower frequency alternating current, or a direct current (DC), to measure oil quality. The system may comprise a single sensor that is used to measure both oil quality (by providing the lower frequency alternating current or direct current) and oil level (by providing the higher frequency alternating current). Using the lower frequency AC, or DC, enables the resistance of the oil to be determined, which gives an accurate indication of the oil quality.

16 Claims, 4 Drawing Sheets

(56) References Cited

U.S. PATENT DOCUMENTS

| | | | |
|---|---|---|---|
| 5,929,754 | A | 7/1999 | Park et al. |
| 6,250,152 | B1 | 6/2001 | Klein et al. |
| 7,729,870 | B2 * | 6/2010 | Sun .................................. 702/52 |
| 2002/0125899 | A1 * | 9/2002 | Lvovich et al. ............... 324/698 |
| 2010/0180663 | A1 | 7/2010 | Sun |
| 2011/0113878 | A1 * | 5/2011 | Ohshima ............... G01F 23/266 73/304 C |

FOREIGN PATENT DOCUMENTS

| | | | | |
|---|---|---|---|---|
| FR | | 2737297 A1 * | 1/1997 | ............ G01F 23/266 |
| WO | WO 2010/092055 A1 | | 8/2010 | |

OTHER PUBLICATIONS

Dec. 18, 2012 Search Report issued in European Patent Application No. EP 12 18 1357.

* cited by examiner

OIL SENSOR

CROSS-REFERENCE TO RELATED APPLICATIONS

This application is based upon and claims the benefit of priority from British Patent Application Number filed 1116173.4 filed 20 Sep. 2011, the entire contents of which are incorporated by reference.

BACKGROUND OF THE INVENTION

1. Field of the Invention

The present invention relates to a method and apparatus for monitoring lubricants in an engine. In particular, the present invention relates to monitoring the level and quality of a lubricant, such as oil, in an engine.

During use, engines, such as gas turbine engines, require lubrication. For example, lubrication may be required to reduce the wear of internal parts that move relative to each other and/or to reduce the friction between such components. Typically, therefore, an engine is provided with a lubrication system, which may comprise one or more pumps and ducts to deliver a lubricant to the desired position in the engine.

Any suitable lubricant may be used, such as oil. The oil/lubricant may contain various additives, such as stabilizers, which may be intended to improve performance of the oil (for example by further reducing friction between lubricated components and/or increasing the temperature range over which the lubricant is effective) and/or to increase the useful life of the lubricant.

2. Description of the Related Art

In order for the lubrication system to perform as intended, the amount (or volume) of lubricant in the system typically needs to be maintained at or above a certain level. Thus, during use, the oil level may be monitored. In some systems, this may be performed using an oil level probe that is inserted into a part of the lubrication system, such as a tank which contains some of the oil in the system.

An oil level probe may operate by supplying an alternating current (AC) to a set of electrodes that are at least partially submerged in the oil whose level is to be measured, and then calculating the capacitance between the electrodes. The capacitance between the electrodes is a function of the depth to which the electrodes are immersed in oil, because the dielectric strength of the oil is different to the dielectric strength of the gas surrounding the non-submerged portion of the electrodes. Thus, the oil level can be determined by the calculated capacitance between the electrodes to which the AC is supplied.

The quality of the lubricant is also important in ensuring that the lubrication system operates in the intended manner. In this regard, typically the lubricant may degrade over time. This may be due to, for example, degradation resulting from temperature cycles and/or from contamination from the parts being lubricated. Modern engines tend to use less oil than their predecessors, meaning that oil tends to remain in the lubrication system for longer periods of time, and thus may need to resist degradation for longer periods of time. Furthermore, some modern engines may run at higher temperatures than their predecessors, which may lead to an increase in the rate of degradation of the oil. As a result, it is advantageous to be able to monitor oil/lubricant quality, or degradation, in the lubrication system, as well as oil/lubricant level. Furthermore, it is desirable to be able to monitor the oil/lubricant quality (as well as level) remotely.

OBJECTS AND SUMMARY OF THE INVENTION

Typically in an engine, such as a gas turbine engine, it is important to minimize the size and/or weight of components. As such, it is still further desirable to provide a small and/or lightweight system/method for monitoring oil quality, as well as oil level.

According to the invention, there is provided a method of measuring both oil (or any lubricant) level and oil (or any lubricant) quality using an oil sensor. The oil sensor comprises a plurality of electrodes. The method comprises placing the oil sensor into oil. The method comprises providing a first current, which is AC at a first frequency, between electrodes (for example at least two pairs of electrodes) of the oil sensor. The method comprises measuring, at the first current, a capacitance parameter representative of the capacitance between the electrodes between which the first current is provided. The capacitance parameter may be, for example, a voltage output from the electrodes in response to the first current. The method may comprise calculating (for example from the representative capacitance parameter), at the first current, the capacitance between the electrodes between which the first current is provided. The level of the oil in which the sensor is placed may then be determined from the measured capacitance parameter, for example from the calculated capacitance. The method comprises providing a second current between electrodes of the sensor. The second current may be provided at a different time to the first current. The second current is either: i) DC (direct current); or ii) AC at a second frequency which is lower than the first frequency. The method comprises measuring, at the second current, an impedance parameter (in the case of an AC second current) or resistance parameter (in the case of a DC second current) representative of the impedance or resistance between the electrodes between which the second current is provided. The impedance or resistance parameter may be, for example, a voltage output from the electrodes in response to the second current. The method may comprise calculating (for example from the impedance or resistance parameter) the impedance or resistance at the second current between the electrodes between which the second current is provided. The method comprises determining the quality of the oil in which the sensor is placed from the measured impedance or resistance parameter, for example from the calculated impedance or resistance.

There is also provided a system (which may be referred to as a device or apparatus) for measuring oil (or any lubricant) level and quality. The system comprises an oil sensor comprising a plurality of electrodes. One or more (for example 2, 3, or more than 3) of the electrodes may be configured to be at least partially submerged in oil when the system is in use. The system comprises a switching mechanism (which may be referred to as a switching unit) configured to switch between a first current and a second current to be provided between electrodes of the oil sensor. The first current is AC at a first frequency, and the second current is either: i) DC; or ii) AC at a second frequency which is lower than the first frequency. The system comprises an oil level calculation unit configured to determine the level of the oil in which the sensor is placed. The oil level calculation unit may determine the oil level by measuring, at the first current, a capacitance parameter representative of the capacitance between the electrodes between which the first current is provided. The oil level calculation unit may calculate (for example from the measured capacitance parameter), at the first current, the capacitance between the electrodes between which the first current is provided. The oil level calculation unit may be an integrated unit or may contain separate elements, for example an element to measure the capacitance and an element to convert the measured capacitance into an oil level reading. The sensor comprises an oil quality calculation unit configured to determine the quality of the oil in which the sensor is placed. The oil quality calculation unit may calculate the oil quality by measuring, at the second current, an impedance parameter or resistance parameter representative of the resistance or impedance between the first electrode and said one of the second or third electrodes. The oil quality calculation unit may calculate (for example from the impedance parameter or resistance parameter), at the second current, the impedance (in the case of an AC second current) or resistance (in the case of a DC second current) between the electrodes between which the second current is provided.

Providing a lower frequency AC (or a DC) to measure oil quality compared with the current frequency used to measure oil level results in a system and method that allows accurate measurement of both oil level and quality. As described herein, the inventors have determined that using a reduced frequency (or DC) so as to determine impedance (or resistance) of the oil results in an accurate oil quality measurement. Using relatively higher frequencies so as to determine capacitance results in an accurate oil level measurement. Such a system and method allows a single system (or probe) to be used to determine accurately both oil level and quality. This may result in reduced mass and/or size, for example compared with a system in which the oil level and quality is determined using at least partially separate systems.

Where the term "oil" is used herein, this could be used to refer to any lubricant, or any other suitable liquid whose level and quality may require monitoring. Reference to the "quality" of the oil may refer to the deterioration of the oil, for example with respect to a baseline, or an original quality. Additionally or alternatively, it may refer to the quality of the oil with respect to a minimum specified quality.

The oil sensor may comprise a first electrode, a second electrode, and a third electrode. The first current may be provided between the first electrode and the second electrode. The first current may also be provided between the first electrode and the third electrode. The second current may be provided between the first electrode and one of the second and third electrodes.

Using such a configuration, the method may comprise measuring/calculating the capacitance parameter, at the first current, between the first and second electrodes and between the first and third electrodes. The measured capacitance parameters may be used to determine the capacitance between the first and second electrodes and between the first and third electrodes. The level of the oil in which the sensor is placed may be determined by comparing the capacitance between the first and second electrodes with the capacitance between the first and third electrodes. In the system for measuring oil level and quality, the oil level calculation unit may be configured to determine the oil level by comparing, at the first current, the capacitance between the first and second electrodes with the capacitance between the first and third electrodes.

Also using such a configuration, the impedance or resistance may be calculated/measured at the second current between the first electrode and said one of the second or third electrode. In the system for measuring oil level and quality, the oil quality calculation unit may be configured to determine the quality of the oil by measuring, at the second current, the impedance or resistance between the first electrode and said one of the second or third electrodes.

Configuring the oil sensor with three electrodes in the manner described above may be a particularly convenient, for example compact and/or lightweight, arrangement. An oil sensor arranged in this way may provide two sets (or pairs) of electrodes. For example, one set of electrodes (which may, for example, be formed between the first and third electrodes) may act as an oil level reference set of electrodes when measuring the oil level. Measurement/calculation of the capacitance between this reference set of electrodes may compensate for any change in the oil properties (for example quality and/or temperature and/or composition) when measuring the capacitance between an oil level measurement pair of electrodes (which may, for example, be formed between the first and second electrodes). The oil quality may then be determined using the same electrodes (for example one or more of the same pair of electrodes) as the reference/measurement pair of electrodes used for determining the oil level, resulting in a compact and/or lightweight and/or robust arrangement.

In a system or method having first, second, and third electrodes, the first electrode may be an elongate electrode having a longitudinal axis. The longitudinally extending surfaces of the first electrode may at least partially surround the second electrode and at least partially surround the third electrode.

The first electrode may have a distal end which, in use, extends furthest into the oil. The third electrode may be surrounded by a distal end portion of the longitudinally extending surfaces of the first electrode. The second electrode may be surrounded by substantially the rest of the longitudinally extending surfaces of the first electrode. The second and third electrodes may be longitudinally separated by a non-conductive spacer. In some arrangements, the only part of the longitudinally extending surfaces of the first electrode that do not is surround the second electrode or the third electrode may surround the non-conductive spacer.

The longitudinally extending surfaces may be surfaces that extend along the major, or longitudinal, axis of the first electrode. The longitudinally extending surfaces of the second and third electrodes may be surrounded by, or at least substantially surrounded by, the longitudinal axis of the first electrode. This may mean that the second and third electrodes are formed by one or more surfaces offset from the longitudinally extending surface of the first electrode. The distal end of the sensor may remain open, for example to allow oil to enter.

In such an arrangement, the first electrode and the second electrode may form a first coaxial electrode pair. The first electrode and the third electrode may form a second coaxial electrode pair.

In some arrangements, the first electrode may be substantially cylindrical. In some arrangements, the second electrode may be substantially cylindrical. In some arrangements, the third electrode may be substantially cylindrical. The first, second, and third electrodes may be concentric. Thus, the first coaxial electrode pair may be concentric and have an annular gap between the electrodes. The second coaxial electrode pair may be concentric and have an annular gap between the electrodes.

The second coaxial electrode pair may form a reference electrode pair for the oil level sensor when the first current is supplied. The first coaxial pair may form a measurement electrode pair when the first current is supplied. The capacitance of the first coaxial electrode pair and the second coaxial electrode pair when the first current is supplied may be used to determine oil level. The second coaxial pair may form an electrode pair between which the impedance or resistance (or a parameter representative thereof) is measured when the second current is supplied in order to determine oil quality.

In a system or method having first, second, and third electrodes, the first electrode may thus be a substantially hollow elongate electrode having a longitudinal axis. The second and third electrodes may be longitudinally aligned within longitudinally extending surfaces of the first electrode. The second and third electrodes may be longitudinally separated by a non-conductive spacer. In such an arrangement, the electrodes may be coaxial. The electrodes may be substantially cylindrical. The electrodes may be concentric. Arranging the second and third electrodes within, which may mean inside and/or surrounded by, the first electrode may be a particularly convenient and compact arrangement.

The second frequency may be less than 1 kHz. For example, the second frequency may be less than 100 Hz, 90 Hz, 80 Hz, 70 Hz, 60 Hz, 50 Hz, 40 Hz, 30 Hz, 20 Hz, 10 Hz, 5 Hz, 2 Hz, or 1 Hz. The second frequency may be DC. Using a second frequency below these values results in a more accurate determination of oil quality (or deterioration). The lower the (second) frequency used, the more accurate may be the determination of oil quality. The first frequency may be greater than 1 kHz, although other frequencies may be used. In general, higher the (first) frequency used, the more accurate may be the determination of oil level.

The inventors have determined that DC resistivity, or low frequency AC impedance, is more sensitive to oil quality deterioration than dielectric strength, which may be determined from capacitance at higher frequencies. Without being bound by any particular theory, this may be due to a greater impact of increased acidity and/or to antioxidant additive depletion on resistivity/low frequency impedance than on dielectric strength.

In an arrangement of oil sensor comprising three sensors, when the oil sensor is placed into the oil, the third electrode may be fully submerged in the oil. For example, the third electrode may be fully submerged (or entirely covered) by the oil even when the oil level is below, for example significantly below, the minimum desired level. Submerging the third electrode in the oil at all times during operation means that the third electrode can be used as part of a reference electrode pair (for example by forming an electrode pair with at least a part of the first electrode) for the oil level sensor. Because the reference electrode pair is fully submerged in the oil at all times, it can accurately compensate for any changes in oil properties.

The second current may be provided between the first electrode and the third electrode. This may mean that the second current is provided between the third electrode and at least a part of the first electrode. This may mean that the second current is provided between the same electrodes (or portions thereof) as the ones that form the reference electrode pair for the oil level sensor. Thus, the oil quality may be determined using the same electrodes that are used as reference electrodes when determining the oil level. This may result in a particularly compact, lightweight, and accurate system.

Alternatively or additionally, the second current may be provided between the first electrode and the second electrode. This may mean that the second current may be provided between the second electrode and at least a portion of the first electrode. This may mean that the second current may be provided between electrodes (or portions thereof) that are not completely submerged in the oil. In this case, the determined level of oil in which the sensor is placed may be used in combination with the impedance measured between the first electrode and the second electrode in order to determine the quality of the oil in which the sensor is placed. In this way, the fact that the pair of electrodes may not be entirely submerged in the oil when measuring the impedance at the second current can be compensated for by the known oil level.

In systems and methods in which the second current is DC, the polarity of the DC current may be reversed each time it is provided compared with the previous time it was provided. This means that a given DC second current may be provided with an opposite polarity to the directly preceding DC second current. This may be achieved by switching the polarity of the electrodes between which the second current is provided. Rather than reversing the polarity each time the second, DC, current is provided, the polarity could be reversed after a set number of provisions of the second current and/or after a set period of time and/or at a particular point during the cycle of an engine on which the system/method is to be applied, such as during engine start-up or shut-down.

Reversing the polarity of a DC second current may reduce and/or eliminate electrode contamination (which may result in performance degradation) over time. It may help to reduce the wear rate of the electrode(s), and thus help to prolong the working life of the sensor. Reversing the polarity may achieve this by reversing any chemical reactions occurring at the electrodes.

The sensor may be placed into oil in an oil tank of an engine. The engine may be of any type that uses a lubrication system. For example, the engine may be an internal combustion engine or a gas turbine engine. The second current may be provided a finite number of times to determine the oil quality at one or more specific times between when the engine is switched on and turned off. Between the finite times when the second current is provided, the first current may be provided substantially continuously during engine running to determine oil level substantially continuously during engine running.

For example, the second current may be provided fewer than 10 times between when the engine is switched on and turned off, for example 9, 8, 7, 6, 5, 4, 3, or 2 times, or once. This may mean that the oil quality is monitored a discreet number of times during use of the engine. This may provide a trend of oil quality over time, for example to assist with determining when an oil change might be required. The first current may be provided for the majority of the time, for example for more than 50% of the time that the engine is turned on, for example more than 75%, more than 90%, more than 95%, or more than 99%. This may mean that the oil level may be monitored continuously, or substantially continuously, during use of the engine.

In use, the sensor may be placed into an oil tank of a gas turbine engine. The second current may be provided upon start-up and/or shut-down of the engine.

The first current may be provided at substantially all other times of engine operation.

In this regard, providing the second current upon start-up of the engine may mean that it is provided just before or just after, for example within a few minutes before or after, start-up of the engine, for example during or just after the engine is spooled up. Similarly providing the second current upon shut-down of the engine may mean providing the second current just before or just after, for example within a few minutes before or after, shut-down of the engine. Providing the first current at substantially all other times means that the oil level may be substantially continuously monitored during engine use. There may, however, be some periods of engine use when the first current is not provided, and thus the oil level is not monitored. For example, there may be some periods, which may be short, when neither the first nor the second current is provided, although in some embodiments either the first or second current may be provided at all times during engine use.

The switching mechanism in the system may contain switching logic to determine when to switch between the first current and the second current. Such switching logic may be contained within the switching mechanism, for example within a switching unit, which may be a separate switching unit or an integral switching unit. The switching logic may ensure that the switching between the first and second currents occurs at the desired time. The switching logic may, for example, switch from the first current to the second current in response to one or more events and/or sensor readings, and/or based on predetermined time intervals.

The system and method may be for use with a gas turbine engine for use on an aircraft. The switching logic may, for example, determine when to switch between the first current and the second current based on one or more of: engine rotational speed, throttle angle, flight phase of the aircraft, and weight on wheels (which may be part of landing gear) of the aircraft. Using such parameters may help to ensure that the oil level and oil quality readings are taken at the most appropriate times during the engine use and/or flight phase.

BRIEF DESCRIPTION OF THE DRAWINGS

Embodiments of the invention will now be described by way of example only, with reference to the accompanying diagrammatic drawings, in which.

DETAILED DESCRIPTION OF THE PREFERRED EMBODIMENTS

A typical engine includes a lubrication system. The lubrication system may provide lubricants, such as oil-based and/or synthetic-based lubricants to a number of different parts of the engine. Indeed, where reference is made herein to oil, it will be appreciated that this means any suitable fluid, such as any lubricant. The terms oil and lubricant are interchangeable herein.

The lubrication system may provide a lubricant to reduce the friction between parts which, in use, may move relative to each other and may rub against each other. This may help to improve performance and/or life of components within the engine. Such lubrication systems may be provided to any type of engine, for example internal combustion engines and gas turbine engines. If the type and/or amount (for example mass flow rate) of oil provided to particular parts of the engine is outside design specification, this may lead to increased wear and/or friction, which may lead to reduced life and/or performance Thus, in order for the engine to perform in the intended manner, the amount of oil, i.e. the oil level, needs to be correct, or at least within design specification. Furthermore the quality of the oil also needs to be within design specification in order for the engine to perform in the intended manner.

Therefore, it is important to be able to monitor accurately the oil level and the oil quality (for example the degree of oil deterioration) in an oil system of an engine. Accurate and efficient monitoring of oil level and quality may increase the amount of preventative, or prophylactic, maintenance compared with the amount of remedial maintenance. It may also be advantageous to be able to monitor the oil level and quality with minimal additional weight. This may be particularly important when monitoring the oil in a gas turbine engine used on a moving vehicle, such as a car or an aircraft, where minimizing weight is an important factor.

Oil quality may reduce over time and/or through engine use. For example, the oil may degrade due to heat and/or pressure cycles, and/or contamination (for example from parts of engine components or reaction with the engine components or other fluids in the engine, including working fluids). Oil consists of an ester basestock to which various chemicals known additives are added. These additives have several functions, for example to protect the basestock, to protect the transmission system and/or to enhance the performance of the oil. The antioxidant additives reduce the amount of oxidation the basestock experiences, but do not stop it all together. Normal engine use imposes thermal stress on the oil which results in chemical changes including the production of acidic species. Thus, as the oil degrades, the acidity of the oil increases.

The acidity of the oil may therefore be indicative of the oil's condition/quality, for example the level of oil degradation. The inventors of the present invention have identified a system and method for accurately measuring the change in the oil's properties. Without being bound by any particular theory, the present system and process may give accurate oil quality readings through measuring changes in electrical properties of the oil, such as resistivity and complex impedance, that result from the change in acidity of the oil.

Figure 1:
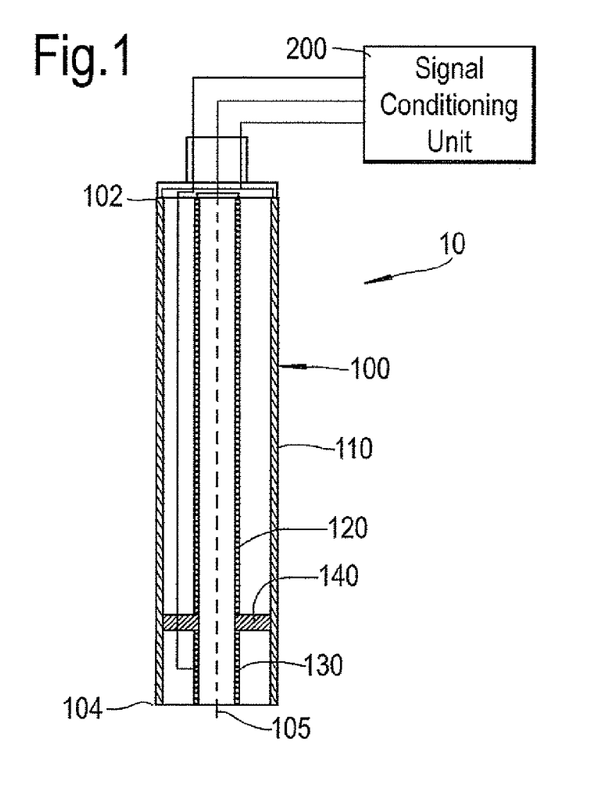
FIG. 1 shows a cross-section through an oil measurement system, including an oil sensor.

FIG. 1 shows an example a system 10 for measuring oil level and quality according to the invention. FIG. 1 shows, in cross-section an example of a sensor (which may be referred to as a probe) 100 that could be used in an oil level and quality measuring system 10. FIG. 1 also shows an example of a signal conditioning unit (SCU) 200 that could be used in an oil level and quality measuring system 10. An example of the SCU 200 is shown in more detail in FIGS. 5 and 7.

The sensor 100 has a first electrode 110, a second electrode 120, and a third electrode 130. The first electrode 110 has a longitudinal axis 105. In the FIG. 1 embodiment, the second electrode 120 and the third electrode 130 also have a longitudinal axis 105, that is the same as the longitudinal axis 105 of the first electrode 110. Thus, any two or more of the first, second and third electrodes 110, 120, 130 may be said to be coaxial.

The first electrode 110, the second electrode 120 and the third electrode 130 is each have a substantially cylindrical shape in the FIG. 1 embodiment. One or more of the first, second, and third electrodes 110, 120, 130 may have shapes that are not cylindrical in some embodiments. For example, one or more of the electrodes may have cross-sections in a plane normal to the longitudinal axis 105 that are triangular, square, pentagonal, hexagonal, or any other regular or irregular shape.

In FIG. 1, the first electrode 110 has a longitudinally extending surface. Indeed, in FIG. 1, the longitudinally extending surface is the cylindrical surface that is axisymmetric about the longitudinal axis 105. The longitudinally extending surface extends from a proximal end 102 of the sensor 100 to a distal end 104 of the sensor 100. As described herein, in use, the distal end 104 of the sensor 100 is inserted into the oil first. In embodiments that do not have a circular cross-section in a plane normal to the longitudinal axis 105, the first electrode may have more than one longitudinally extending surface.

Each of the second electrode 120 and the third electrode 130 also has a longitudinally extending cylindrical surface in the FIG. 1 embodiment. In the FIG. 1 embodiment, the second electrode 120 and the third electrode 130 are coaxial, concentric cylinders that are axially separated by a spacer 140. The spacer 140 may be a non-conductive co-axial spacer 140.

The second electrode 120 forms a first electrode pair with the first electrode 110. In the FIG. 1 embodiment, the first electrode pair is formed between a proximal end portion of the first electrode 110 and the second electrode 120. Thus, the first electrode pair in FIG. 1 comprises concentric, cylindrical electrodes 110, 120. The second electrode 120 may thus be said to be surrounded by a portion, for example a proximal or upper portion, of the first electrode 110.

The third electrode 130 forms a second electrode pair with the first electrode 110. In the FIG. 1 embodiment, the second electrode pair is formed between a distal end portion of the first electrode 110 and the third electrode 130. Thus, the second electrode pair in FIG. 1 comprises concentric, cylindrical electrodes 110, 130. The third electrode 130 may thus be said to be surrounded by a portion, for example a distal or lower portion, of the first electrode 110.

Figure 2:
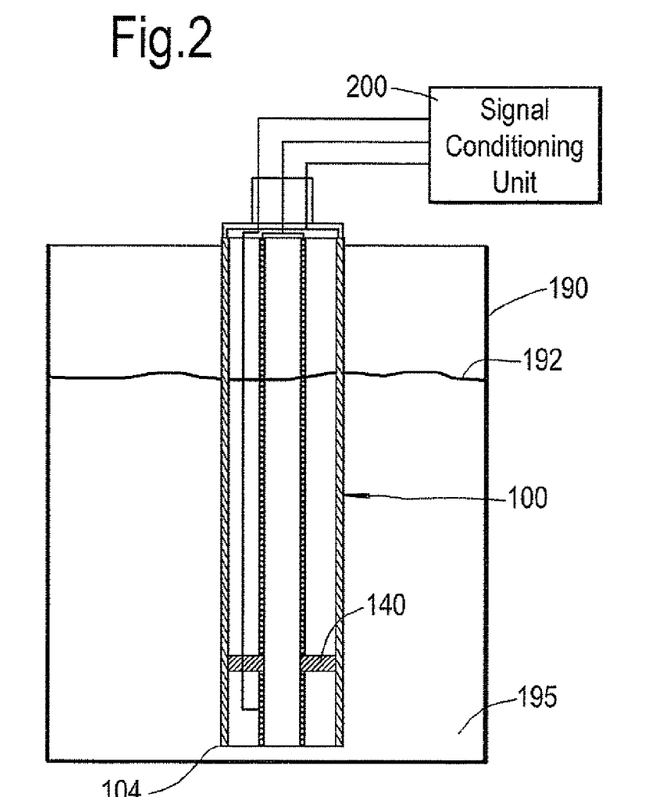
FIG. 2 shows a the system of FIG. 1 with the sensor placed in a lubricant.

FIG. 2 is a schematic showing the sensor 100 inserted into a container, such as a tank, 190 containing a liquid, such as lubricant, such as oil 195. The lubricant 195 partially fills the tank 190, such that the lubricant 195 has an open surface 192. The method and system according to the present invention may allow the level of oil 195 in the tank and the quality of the oil in the tank to be measured accurately and easily, for example using a single sensor 100.

As shown in FIG. 2, the oil 195 enters the sensor 100 through the distal end 104 of the sensor 100. This may be possible due to the electrodes 110, 120, 130 having at least partially open (distal) ends. Thus, in the FIG. 2 embodiment, one or more of the electrodes 110, 120, 130 may be referred to as open cylinders. Although the cross section of FIGS. 1 and 2 does not show a flow path for the oil to reach the gap between the first electrode 110 and the second electrode 120, a suitable flow path is provided in the FIG. 3 embodiment, for example in a plane other than that shown in cross section in FIGS. 1 and 2. For example, a lubricant flow path may be provided as one or more gaps in the spacer 140 and/or one or more suitable gaps in the third electrode 130.

Figure 3:
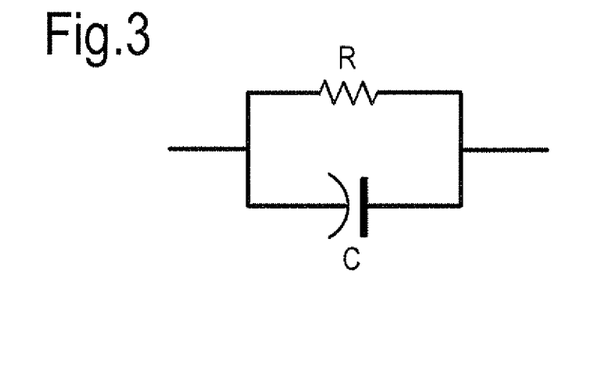
FIG. 3 shows an equivalent circuit representing an electrode pair with a lubricant between the electrodes.

When an AC signal is provided to an electrode pair of the sensor 100, the response can be represented by an equivalent circuit of a capacitor in parallel with a resistor, as shown in FIG. 3. This equivalent circuit may be applicable to, for example, the electrode pair formed between the first resistor 110 and the second resistor 120, and also to the electrode pair formed between the first resistor 110 and the third resistor 130.

As is well known in the art, the complex impedance z (or response) for such an equivalent circuit (shown in FIG. 3) is given by:

$$z = \frac{R}{1 + j2\pi fCR} \quad \text{(Equation 1)}$$

Where:
z is the complex impedance
R is the resistance of the resistor in the equivalent circuit
C is the capacitance of the capacitor in the equivalent circuit
f is the frequency of the AC At sufficiently low frequency AC, the j2πfCR term becomes much less than 1, and so the magnitude of equation (1) above becomes:

$$|z| \approx R \text{ (low frequencies)}$$

Thus, the response of the electrode pairs to sufficiently low frequency AC becomes proportional to the resistance of the equivalent circuit. Of course, when DC is supplied, the capacitor no longer appears in the equivalent circuit of FIG. 3, and the response is proportional to the resistance R.

As explained above, the inventors have revealed that the resistance of oil may be used as an accurate and/or sensitive indicator of oil quality. Thus, by supplying low frequency AC (for example low enough that the term j2πfRC is sufficiently less than 1 that it can be ignored) or DC current to an electrode pair formed by the first electrode 110 with either the second electrode 120 or the third electrode 130, the response (for example a measured output voltage) may be used as an indicator of oil quality and/or deterioration.

Figure 8:
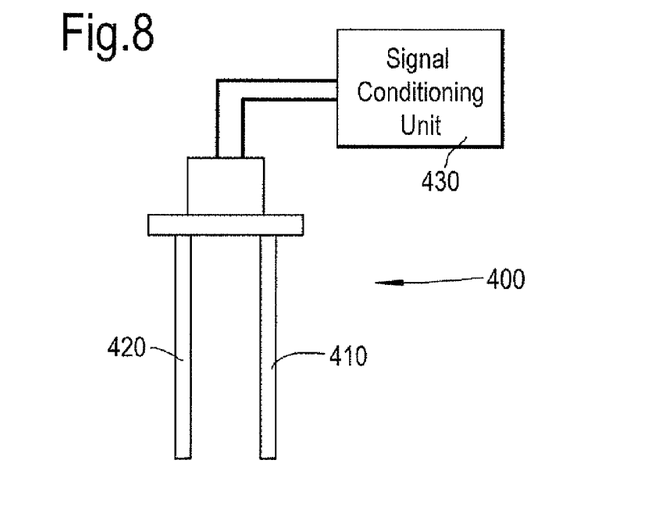
FIG. 8 shows a sensor for measuring oil quality.

A device for measuring the resistance, and thus quality, of a liquid, such as oil, is shown in FIG. 8. The FIG. 8 arrangement has a first electrode 410, a second electrode 420, and a signal conditioning unit 430. In operation, the first and second electrodes may be at least partially submerged in oil, and a DC signal may be supplied to them from the signal conditioning unit 430. The resistance of the oil may then be determined, for example using a known resistor and voltage divider in the signal conditioning unit 430. The measured resistance may then be used to determine oil quality/deterioration.

Returning now to Equation 1, at sufficiently high frequency AC, the j2πfCR term becomes much greater than 1, and so the magnitude of equation (1) above becomes:

$$|z| \approx \frac{1}{2\pi fC}$$

Thus, at high frequency AC, the response of the electrode pairs becomes inversely proportional to the capacitance of the equivalent circuit. The capacitance between two electrodes 110, 120, 130 that form an electrode pair is indicative of the level of oil between the electrodes. For example, the dielectric strength of the oil may be very different to the dielectric strength of the gas above the oil in the tank, and so the capacitance may give a good indication of the level to which the electrodes are submerged in oil.

As such, supplying a high frequency AC to suitable electrode pair(s) of the sensor 100 may give a response indicative of oil level. Supplying a suitably low (or lower) AC, or a DC, signal to suitable electrode pair(s) of the sensor 100 may give a response indicative of oil quality.

Figure 4:
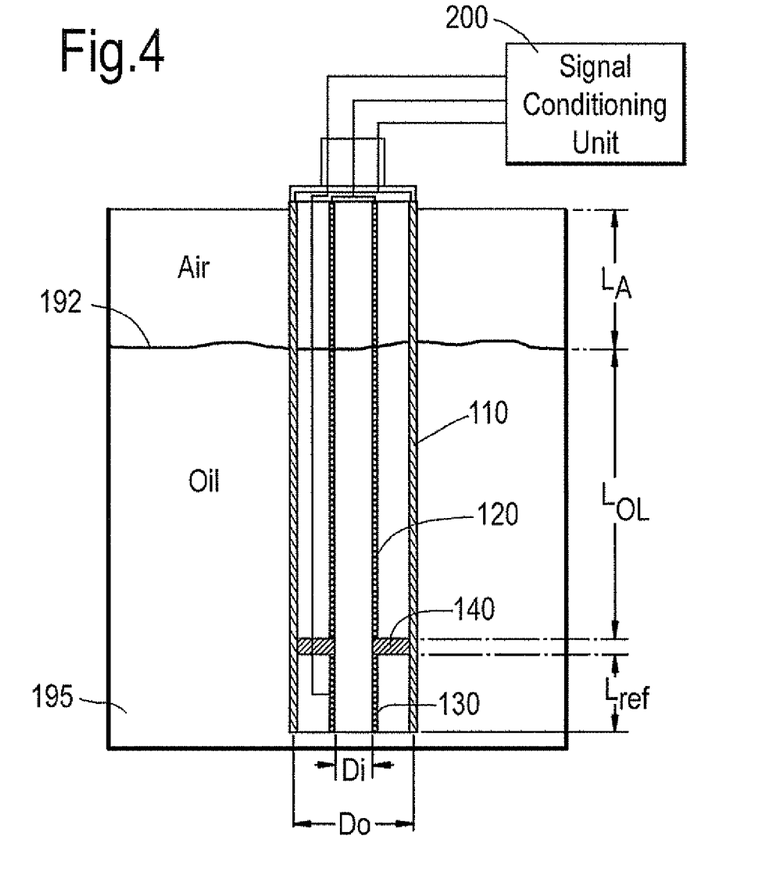
FIG. 4 shows the system of FIG. 1 with the sensor placed in a lubricant, including dimension labels.

FIG. 4 shows an embodiment such as that of FIGS. 1 and 2 immersed in a lubricant 195, with the addition of dimension references $L_A$, $L_{OL}$, $L_{ref}$, $D_o$ and $D_i$. The length $L_{OL}$ is the length of the electrode pair formed between the first electrode 110 and the second electrode 120 that is submerged in oil, and the length $L_A$ represents the length of that electrode pair (formed between the first electrode 110 and the second electrode 120) that is not submerged in oil, i.e that is surrounded by gas (such as air) in the tank 190. The length $L_{ref}$ is the length of the electrode pair formed between the first electrode 110 and the third electrode 130, which is completely submerged in the oil 195. $D_o$ is the diameter of the first electrode 110, and $D_i$ is the diameter of both the second electrode 120 and the third electrode 130. These references will be used in the explanation below of the operation of this embodiment.

Figure 5:
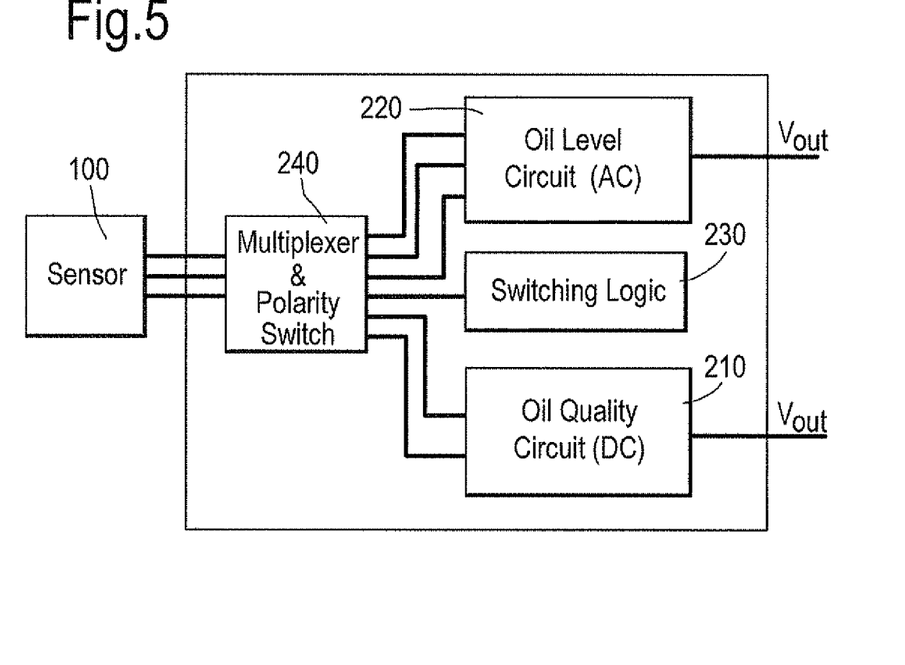
FIG. 5 shows the system of FIG. 1, with an example of the signal conditioning unit shown in greater detail.

FIG. 5 shows the signal conditioning unit 200 of FIGS. 1, 2, and 4 in greater detail. In particular, FIG. 5 shows an oil quality circuit 210, an oil level circuit 220, switching logic 230, and a multiplexer and polarity switch 240. These features are described in greater detail below.

Figure 6:
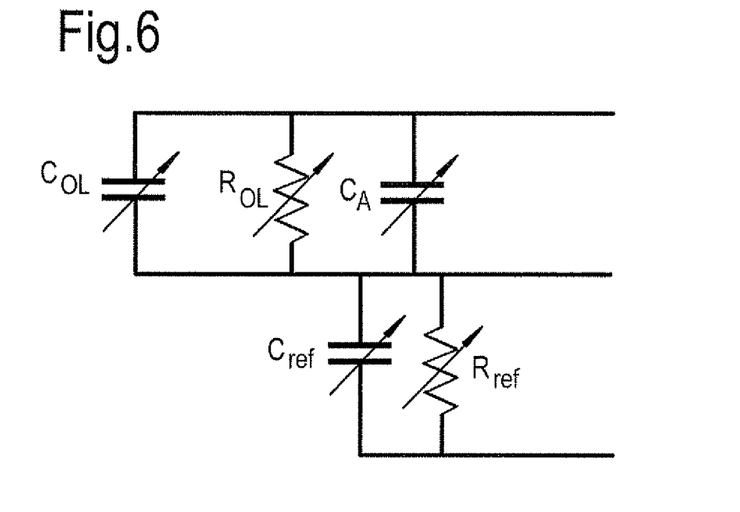
FIG. 6 shows an equivalent circuit for a sensor.

FIG. 6 shows an equivalent circuit for the electrode arrangement partially submerged in oil shown in FIG. 4. In FIG. 6, the capacitor $C_{OL}$ and the resistor $R_{OL}$ correspond to the length $L_{OL}$ of the first electrode pair formed by the first electrode 110 and the second electrode 120 that is submerged in oil 195. The capacitor $C_A$ represents the length $L_A$ of the first electrode pair formed by the first electrode 110 and the second electrode 120 that is not submerged in oil. The capacitor $C_A$ is thus shown in parallel with the capacitor $C_{OL}$ and the resistor $R_{OL}$. The capacitor $C_{ref}$ and the resistor $R_{ref}$ correspond to the length $L_{ref}$ of the second electrode pair (which may be referred to as a reference electrode pair) formed by the first electrode 110 and the third electrode 130. As shown in FIG. 4, this second electrode pair is totally submerged in oil 195.

Turning firstly to the measurement of oil level/volume (which may be determined readily from the value of $L_{OL}$), this may be determined from the capacitance ($C_{OL}$) of the part of the sensor that is immersed in oil. As noted above in relation to FIG. 3, this may be determined by supplying a high frequency AC to the electrode pair formed by the first and second electrodes 110, 120. However, supplying a high frequency AC to the electrode pair formed by the first and second electrodes 110, 120 actually results in a measurement of the combined capacitance $C_L$ of the part of the electrode pair immersed in oil ($C_{OL}$) as well as the part of the electrode pair exposed to the air in the tank ($C_A$), i.e.:

$$C_L = C_{OL} + C_A$$

Thus:

$$C_L = \frac{2\pi\varepsilon_{oil} L_{OL}}{\ln\left(\frac{D_o}{D_i}\right)} + \frac{2\pi\varepsilon_{air} L_A}{\ln\left(\frac{D_o}{D_i}\right)}$$

Where:
$\varepsilon_{oil}$ is the dielectric strength of the oil; and
$\varepsilon_{air}$ is the dielectric strength of the air.

If L represents the total length of the first electrode pair (i.e. the length of the second electrode 120), such that $L_A = L - L_{OL}$, then:

$$C_L = \frac{2\pi\varepsilon_{oil} L_{OL}}{\ln\left(\frac{D_o}{D_i}\right)} + \frac{2\pi\varepsilon_{air} (L - L_{OL})}{\ln\left(\frac{D_o}{D_i}\right)} \quad \text{(Equation 2)}$$

Thus:

$$L_{OL} = \frac{C_L - \frac{2\pi\varepsilon_{air} L}{\ln\left(\frac{D_o}{D_i}\right)}}{\frac{2\pi\varepsilon_{oil}}{\ln\left(\frac{D_o}{D_i}\right)} - \frac{2\pi\varepsilon_{air}}{\ln\left(\frac{D_o}{D_i}\right)}}$$

The dielectric strength of the oil $\varepsilon_{oil}$ is dependent on a number of variables, such as oil type, condition and/or temperature. The value of the dielectric strength of the oil $\varepsilon_{oil}$ may be determined at the time of measurement using the capacitance $C_{ref}$ between the electrode pair formed by the first electrode 110 and the third electrode 130, which may be referred to as the reference electrode pair, or reference capacitor:

$$\varepsilon_{oil} = \frac{C_{ref} \ln\left(\frac{D_o}{D_i}\right)}{2\pi L_{ref}}$$

Substituting for $\varepsilon_{oil}$ in Equation 2 gives:

$$L_{OL} = \frac{C_L - \frac{2\pi\varepsilon_{air} L}{\ln\left(\frac{D_o}{D_i}\right)}}{\frac{C_{ref}}{L_{ref}} - \frac{2\pi\varepsilon_{air}}{\ln\left(\frac{D_o}{D_i}\right)}} \quad \text{(Equation 3)}$$

Figure 7:
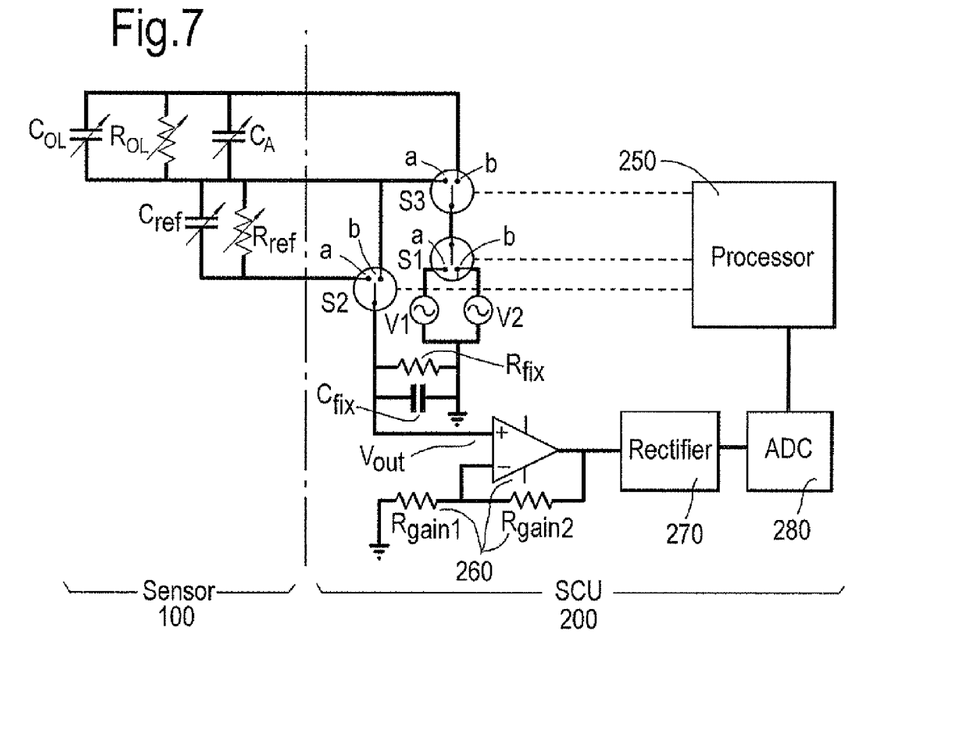
FIG. 7 shows a circuit for obtaining oil level and quality readings from the sensor.

In Equation 3, $\varepsilon_{air}$, L, Do and Di are all known and constant. Thus, in order to calculate the oil level ($L_{OL}$), only $C_L$ and $C_{ref}$ need to be determined. These may be determined using the sensor 100, by supplying appropriate signals and measuring appropriate responses. An example of a circuit that may be used to determine $C_L$ and $C_{ref}$ is shown in FIG. 7. It is emphasised that the circuit and components thereof shown in FIG. 7, and the associated description given herein, is only one example of a circuit and associated method that could be used to determine $C_L$ and $C_{ref}$ (or any other parameters as may be required in alternative embodiments). Many other circuits/components/methods falling within the scope of the invention may be used.

The left hand side of FIG. 7 is an equivalent circuit representing the sensor 100. This equivalent circuit is the same as that shown in FIG. 6 and described above. The right hand side of FIG. 7 represents circuitry of the signal conditioning unit (SCU) 200. It will be appreciated that the SCU 200 may be arranged in any appropriate manner. As such, the components of the SCU 200 may not necessarily be arranged and/or segmented into the multiplexer/polarity switch 240, switching logic 230, oil level circuit 220, and oil quality circuit 210 shown in FIG. 5. However, in some respects, the processor 250 may be considered to comprise the switching logic 230 of FIG. 5; the switches S1, S2, S3 may be considered to be part of the multiplexer/polarity switch 240 of FIG. 5; and the generators V1, V2, the capacitor $C_{fix}$, the resistor $R_{fix}$, and (optionally) the amplifier 260 may be considered to represent the oil level circuit 220 and oil quality circuit 210 in FIG. 5.

In FIG. 7, V1 may be a high frequency AC source with and amplitude $V_H$ and a frequency $f_H$. V1 may be used to determine $C_L$ and $C_{ref}$ in order to calculate the oil level $L_{OL}$, for example using equation 3. V2 may be used to determine oil quality, as explained in greater detail below, and may be a low frequency AC source (at least lower frequency than V1) or a DC source.

S1, S2, and S3 are each two-way switches. $C_{fix}$ is a fixed value capacitor. $R_{fix}$ is a fixed value resistor.

Resistors $R_{gain1}$ and $R_{gain2}$ may be used to adjust the output voltage $V_{out}$ to a suitable level for input into the analogue to digital convertor (ADC) 280. The demodulator (or rectifier) 270 may be used to extract a DC waveform from the voltage output $V_{out}$, and thereby extract the amplitude information from and $V_{out}$ in the event that $V_{out}$ is an AC waveform. The ADC 280 may be used to convert the analogue output from the demodulator 270 to a digital value that may be processed by the processor 250. The processor 250 may contain circuitry and/or logic to output oil level and/or quality readings to a user, for example to a display device that may be read by a user.

It will be appreciated that some of the components shown in FIG. 7 (for example the amplifier 260, the demodulator 270, the ADC 280, and at least a part of the processor 250), and the functions performed by them, may be either within the system 10 (i.e. within the SCU 200), or outside of the oil measurement system 10. Thus, such components (and the functions performed by them) may be either included within the oil measurement system 10, or may be provided by a system/apparatus with which the oil measurement system 10 cooperates/interacts.

In order to calculate the oil level, i.e., in order to calculate $C_L$ and $C_{ref}$, the switch S1 is set to position a.

Then, to determine the value of $C_L$, the switches S2 and S3 are set to position b.

As explained above, $C_L$ is the combined capacitance of the gap between the first and second electrodes 110, 120 filled with air, and the gap between the first and second electrodes 110, 120 filled with oil. In the circuit of FIG. 6 (and FIG. 7), this combined gap is represented by:

$$Zc_L = ZC_{OL} \| R_{OL} \| Zc_A$$

Because V1 is a suitably high frequency AC, $R_{OL}$ can be neglected (as explained in relation to FIG. 3), and so the combined impedance of the oil and air gaps between the first and second electrodes 120, 130 at V1 may be given by:

$$ZC_L = \frac{-j}{2\pi f C_L}$$

Similarly, the fixed resistor $R_{fix}$ that is in parallel with the fixed capacitor $C_{fix}$ may be neglected, and so the combined impedance of $R_{fix}$ and $C_{fix}$ may be given by:

$$ZC_{fix} = \frac{-j}{2\pi f C_{fix}}$$

With S1, S2, and S3 set as above, a voltage divider is produced, which yields $V_{out}$ as:

$$V_{out1} = \frac{Z_{C_{fix}}}{Z_{C_{fix}} + Z_{C_L}} V_H$$

Substituting for $ZC_L$ and $ZC_{fix}$ gives:

$$V_{out1} = \frac{\frac{-j}{2\pi f C_{fix}}}{\frac{-j}{2\pi f C_{fix}} - \frac{j}{2\pi f C_L}} \cdot V_H \quad \text{(Equation 4)}$$

So:

$$C_L = \frac{1}{\frac{V_H}{V_{out1}} - 1} C_{fix}$$

Where:
$V_{out1}$ is the output voltage $V_{out}$ for this particular switch arrangement.

In order to determine $C_{ref}$, the switch S1 is left in position a, and the switched S2 and S3 are also set to position a. The value of the capacitance between the immersed first and third electrodes 110, 130 can then be calculated in an analogous manner, as:

$$C_{ref} = \frac{1}{\frac{V_H}{V_{out2}} - 1} C_{fix} \quad \text{(Equation 5)}$$

Where:
$V_{out2}$ is the output voltage $V_{out}$ for this particular switch arrangement.

The values of $C_L$ and $C_{ref}$ may be stored, for example in a memory of the processor 250. The calculated values of $C_L$ and $C_{ref}$ from Equations 4 and 5 may be substituted into Equation 3 in order to determine the value of $L_{OL}$, and thus the height/volume of oil in the tank.

Turning now to determination of the oil quality, in this embodiment, this may be achieved using only the electrode pair formed by the first electrode 110 and the third electrode 130, i.e. the electrode pair that is fully submerged in oil 195. In order to measure oil quality using the FIG. 7 arrangement, switch S1 is set to position b, and switches S2 and S3 are set to position a. This results in a voltage divider between the electrode pair formed by the first and third electrodes 110, 130 ($R_{ref} \| Zc_{ref}$), and the fixed resistor and capacitor ($R_{fix} \| Zc_{fix}$).

As explained herein, the resistance of a lubricant may be a good indicator of its quality. Thus, V2 is either a DC supply or a sufficiently low frequency AC supply such that the resistance term dominates both $R_{ref} \| Zc_{ref}$ and $R_{fix} \| Zc_{fix}$. Thus, in the event that a DC source is used as V2, the resistance of the oil can simply be calculated as:

$$R_{ref} = \left( \frac{V_{DC}}{V_{out3}} - 1 \right) R_{fix}$$

Where:
$V_{out3}$ is the output voltage $V_{out}$ for this particular switch arrangement.

In the event that a low frequency AC source is used as V2, the complex impedance of the oil is given as:

$$Z_{ref} = \left( \frac{V_L}{V_{out3}} - 1 \right) Z_{fix}$$

Because V2 is a low frequency AC source, the measured value of $Z_{ref}$ is dominated by the resistance of the oil, and thus is still representative of the oil quality.

In order to assess the oil quality from the value of $R_{ref}$ or $Z_{ref}$ any suitable method may be used. For example, the $R_{ref}$ or $Z_{ref}$ value could be converted to an oil quality reading (such as, by way of example only, acidity level). The determined oil quality reading could then be compared with, for example, one or more reference levels, and/or with one or more previous readings. This may give an indication of oil quality and/or of oil quality deterioration rate. Alternatively or additionally, the $R_{ref}$ or $Z_{ref}$ value could be used directly to assess the oil quality. This may be done, for example, by comparing the $R_{ref}$ or $Z_{ref}$ value with one or more reference resistance/impedance readings, and/or with one or more previous resistance/impedance readings. At least one reference resistance/impedance value may represent, for example, a minimum allowable oil quality threshold.

Note that in arrangements, the low frequency AC, or DC, supply V2 for the oil quality measurement may be provided to the first electrode 110 and the second electrode 120. In such embodiments, the calculated oil level (as described herein) may also be used to calculate the oil quality from the resistance/impedance between the first electrode 110 and the second electrode 120.

Also note that, in the example explained above in relation to FIG. 7, the output voltages $V_{out}$ may be examples of capacitance, resistance and/or impedance parameters representative of the capacitance, resistance, or impedance between the relevant electrodes. For example $V_{out1}$ and $V_{out2}$ are examples of capacitance parameters that may represent the capacitance between the first and second electrodes 110, 120, and the first and third electrodes respectively (using the V1 signal). $V_{out3}$ is an example of an impedance or resistance parameter representative of the impedance or resistance between the first and third electrodes (using the V2 signal).

Once again, it will be appreciated that the circuit shown in FIG. 7 is merely an example of many different circuits that could be used to determine oil resistance (in order to determine oil quality) and capacitance (in order to determine oil level). Other possible circuits would readily be apparent to a person of ordinary skill, and any of these other circuits could be used in other embodiments falling within the scope of the claims.

Switching between the positions a and b in the switches S1, S2, and S3 may be on the basis of instructions from switching logic 230 of FIG. 5, which may be a part of the processor 250 of FIG. 7. Thus, the switching logic 230 and switch 240 may determine whether the sensor 100 is being used to measure oil quality or oil level at any given time. For example, the switching logic 230 may contain logic which outputs an instruction to the switch 240 to switch between the oil quality and oil level measurement functions described above.

The instruction from the switching logic 230 may be based on any suitable input and/or calculation. For example, in the event that the oil sensor 100 is used in a gas turbine engine installed in an aircraft, the switching logic may instruct the oil quality measurement to be performed only at certain times during operation of the engine. At all other times, the switching logic may instruct the oil level measurement to be performed. For example, the switching logic may instruct the oil quality measurement to be performed at one or more of the following times: on engine start-up, shortly after engine start-up (for example long enough for the oil to reach operating temperature, as the temperature of the oil may affect the oil quality reading), during flight, just after landing (which may, for example, be sensed using a load sensor on the landing gear), just before engine switch-off, or just after engine switch off. It will be appreciated, however, that the oil quality/level readings could be arranged to be taken at any time. Alternatively or additionally, it may be possible in some embodiments for an operator to manually switch between the oil level and oil quality functions as and when desired.

In some embodiments, the sensor 100 may be used to measure oil level for the majority of the time. The sensor may be used to measure oil quality only for a minority of the time. For example, each oil quality reading may only take a short period of time, for example less than 5 minutes, less than 2 minutes, less than 1 minute, or less than 30 seconds. In an example in which the sensor 100 is used in a gas turbine engine installed on an aeroplane, the oil quality reading may only need to be taken a finite number of times per flight, for example once, twice, three times, four times, five times, between 5 and 10 times, or ten times or more.

In some embodiments, the switching logic 230 may instruct the oil quality measurement after a certain period of time, which may for example be in the range of from 30 minutes to 10 hours, for example 1 hour to 5 hours, for example 2 hours to 4 hours, for example around 3 hours.

The system 10 may be further configured to switch the polarity, for example between readings, of the current provided to the electrodes (for example the first electrode 110 and the third electrode 130) when using a DC signal to determine oil quality. For example, the polarity may be switched between every oil quality reading, or between every two, three, four, five, or more than five readings. The polarity switching may be performed by any suitable means. In FIG. 5, the polarity switching is shown as being performed in the multiplexer and polarity switch 240. However, the polarity switching device may be provided at any suitable position, for example within the signal conditioning unit 200. For example the polarity switching may be performed in the oil quality circuit 210 itself.

An advantage of including polarity switching means is that it may help to reduce and/or prevent damage (such as electroplating and/or degradation) to the electrodes during measurement of the oil quality. This may occur if a DC is supplied to the electrodes during oil quality determination. However, switching the polarity of the DC, for example between measurements, may help to alleviate this potential problem. However, as mentioned herein, the oil quality measurement circuit may only be in use for short periods of time, for example less than the oil level measurement circuit is in use. Thus, electrode damage during oil quality measurements may not be problematic, due to the short periods of time in which the oil quality is measured. As such, polarity switching may not be required, and so some embodiments, which may otherwise be as described herein, may not include polarity switching, or any means therefor.

It will be appreciated that the various parts and/or components of the oil measurement system 10 described herein could take any suitable form and/or arrangement. For example, the sensor 100 and the signal conditioning unit 200 could be provided as a single unit, for example integrated into a single unit. Such a single unit may, for example, have the sensor 100 and the signal is conditioning unit 200 provided in a single housing. Alternatively, at least some of the parts and/or components of the system 10 may be separate from each other, for example provided physically apart, such as in different housings. For example, the sensor 100 may be provided in a different place to the signal conditioning unit 200. The sensor 100 and the signal conditioning unit 200 may communicate with each other remotely, for example through physical wires or through a wireless connection. Any other suitable separation of the features/components of the oil measurement system 10 may be used.

As described above, outputs from the oil measurement system 10 may include a reading relating to the oil quality, and a reading relating to oil level. The outputs may be direct voltages and/or calculated resistance, impedance and/or capacitance. These outputs may be transmitted to a further device (which may or may not be included in embodiments of the invention) where they may be converted into oil level/ quality readings. Alternatively, the outputs may be converted into oil level/quality readings within the oil measurement system 10 itself, for example within the signal conditioning unit 200. Transmission of the output(s) from the oil measurement system 10 to another device may be through any suitable means, for example wired or wireless connection/transmission.

Any suitable sensor 100 may be used with the system and/or method of the invention. Thus, for example, the sensor 100 is not limited to that described herein in relation to FIG. 1. For example, any other suitable configuration of electrodes 110, 120, 130 may be used, and many such alternative arrangements would be readily apparent to the skilled person. Some other embodiments may also comprise three electrodes, whereas other embodiments may comprise a different number of electrodes, such as four or more electrodes. Purely by way of example, any electrode configuration to which the above description and/or calculations would be broadly applicable could be used.

It will be appreciated that many alternative configurations and/or arrangements of the oil measurement system 10 and components/parts thereof other than those described herein may fall within the scope of the invention. For example, alternative arrangements of sensor 100, signal conditioning unit 200, and/or components/parts thereof may fall within the scope of the invention and be is readily apparent to the skilled person from the disclosure provided herein. Furthermore, any feature described and/or claimed herein may be combined with any other compatible feature described in relation to the same or another embodiment.

We claim:

1. A method of measuring lubricant level and quality using a lubricant sensor that comprises a plurality of electrodes, the method comprising:
   placing the lubricant sensor into a lubricant;
   providing a first current, which is AC at a first frequency, (a) between a first electrode and a second electrode of the lubricant sensor and (b) between the first electrode and a third electrode of the lubricant sensor;
   measuring, at the first current, between the first and second electrodes, and between the first and third electrodes, capacitance parameters used to determine the capacitance between the first and second electrodes and the capacitance between the first and third electrodes;
   determining the level of the lubricant in which the sensor is placed from the measured capacitance parameters by comparing the capacitance between the first and second electrodes with the capacitance between the first and third electrodes;
   providing a second current between the first electrode and one of the second and third electrodes, the second current being provided at a different time to the first current and being either: (i) DC; or (ii) AC at a second frequency that is lower than the first frequency;
   measuring, at the second current and between the first electrode and the one of the second and third electrodes, an impedance or resistance parameter representative of the impedance or resistance between the first electrode and the one of the second and third electrodes; and
   determining the quality of the lubricant in which the sensor is placed from the measured impedance or resistance parameter.

2. A method of measuring lubricant level and quality according to claim 1, wherein the second frequency is less than 1 kHz.

3. A method of measuring lubricant level and quality according to claim 1, wherein by placing the lubricant sensor into the lubricant, the third electrode is fully submerged in the lubricant.

4. A method of measuring lubricant level and quality according to claim 3, wherein the second current is provided between the first electrode and the third electrode.

5. A method of measuring lubricant level and quality according to claim 3, wherein:
   the second current is provided between the first electrode and the second electrode; and
   the determined level of the lubricant in which the sensor is placed is used in combination with the impedance parameter measured between the first electrode and the second electrode to determine the quality of the lubricant in which the sensor is placed.

6. A method of measuring lubricant level and quality according to claim 1, wherein:
   the second current is DC; and
   the polarity of the DC is reversed each time it is provided compared with the previous time it was provided.

7. A method of measuring lubricant level and quality according to claim 1, wherein:
   the lubricant into which the sensor is placed is lubricant in a tank of an engine;
   the second current is provided a finite number of times to determine the lubricant quality at one or more specific times between when the engine is switched on and turned off; and
   between the finite times when the second current is provided, the first current is provided substantially continuously during engine running to determine lubricant level substantially continuously during the engine running.

8. A method of measuring lubricant level and quality according to claim 7, wherein:
   the second current is provided upon start-up and/or shutdown of the engine; and
   the first current is provided at substantially all other times of engine operation; and
   the engine is a gas turbine engine.

9. A method of measuring lubricant level and quality according to claim 1, wherein:
   the first electrode is an elongate electrode having a longitudinal axis and at least one longitudinally extending surface; and
   the at least one longitudinally extending surface of the first electrode at least partially surrounds the second electrode and the third electrode.

10. A method of measuring lubricant level and quality according to claim 9, wherein:
    the first electrode has a distal end that, in use, extends farthest into the lubricant;
    the third electrode is surrounded by a distal end portion of the at least one longitudinally extending surface of the first electrode;
    the second electrode is surrounded by substantially the rest of the at least one longitudinally extending surface of the first electrode; and
    the second and third electrodes are longitudinally separated by a non-conductive spacer.

11. A system for measuring lubricant level and quality, comprising:
- a lubricant sensor comprising a plurality of electrodes, one or more of the electrodes being configured to be at least partially submerged in lubricant in use;
- a switching mechanism configured to switch between (a) a first current to be provided between first and second electrodes of the lubricant sensor and between the first electrode and a third electrode of the lubricant sensor, and (b) a second current to be provided between the first electrode and one of the second and third electrodes, the first current being AC at a first frequency, and the second current being either: (i) DC; or (ii) AC at a second frequency that is lower than the first frequency;
- a lubricant level calculator configured to determine the level of the lubricant in which the sensor is placed by measuring, at the first current, between the first electrode and the second electrode, and between the first electrode and the third electrode, the capacitance between the first electrode and the second electrode and the capacitance between the first electrode and the third electrode, and comparing the measured capacitance between the first electrode and the second electrode with the measured capacitance between the first electrode and the third electrode; and
- a lubricant quality calculator configured to determine the quality of the lubricant in which the sensor is placed by measuring, at the second current, an impedance or resistance parameter representative of the impedance or resistance between the first electrode and the one of the second and third electrodes.

12. A system for measuring lubricant level and quality according to claim 11, wherein the switching mechanism contains switching logic to determine when to switch between the first current and the second current.

13. A system for measuring lubricant level and quality according to claim 12, wherein:
- the system is for use with a gas turbine engine for use on an aircraft; and
- the switching logic determines when to switch between the first current and the second current based on one or more of: engine rotational speed, throttle angle, flight phase of the aircraft, oil pressure, and weight on landing wheels of the aircraft.

14. A system of measuring lubricant level and quality according to claim 11, wherein:
- the first electrode is an elongate electrode having a longitudinal axis and at least one longitudinally extending surface; and
- the at least one longitudinally extending surface of the first electrode at least partially surrounds the second electrode and the third electrode.

15. A system of measuring lubricant level and quality according to claim 14, wherein:
- the first electrode has a distal end that, in use, extends farthest into the lubricant;
- the third electrode is surrounded by a distal end portion of the at least one longitudinally extending surface of the first electrode;
- the second electrode is surrounded by substantially the rest of the at least one longitudinally extending surface of the first electrode; and
- the second and third electrodes are longitudinally separated by a non-conductive spacer.

16. A system for measuring lubricant level and quality according to claim 11, wherein the second current is DC.

* * * * *